United States Patent
Lando

(12) 
(10) Patent No.: US 6,253,388 B1
(45) Date of Patent: Jul. 3, 2001

(54) EYE WEAR WITH SNAP-TOGETHER BRIDGE

(76) Inventor: Ronald Lando, 55 Aptos Ave., San Francisco, CA (US) 94127

( * ) Notice: Subject to any disclaimer, the term of this patent is extended or adjusted under 35 U.S.C. 154(b) by 0 days.

(21) Appl. No.: 09/476,587

(22) Filed: Dec. 31, 1999

(51) Int. Cl.[7] .................................................. A61F 9/02
(52) U.S. Cl. .................. 2/445; 2/448; 2/454; 24/303; 351/124
(58) Field of Search ................. 2/426–430, 445–448, 2/454, 452; 351/41, 43, 44, 53, 65, 68, 98, 124, 125, 133, 118; 600/9, 15; 24/303

(56) References Cited

U.S. PATENT DOCUMENTS

| | | | | |
|---|---|---|---|---|
| 466,896 | * | 1/1892 | Warren | 2/426 |
| 871,762 | * | 11/1907 | Meyrowitz | 2/426 |
| 1,254,090 | * | 7/1918 | Troppman | 2/426 |
| 1,760,650 | * | 5/1930 | Kruening | 2/426 |
| 2,128,085 | * | 8/1938 | Fischer | 2/426 |
| 4,479,703 | * | 10/1984 | Enghofer | 351/123 |
| 4,610,519 | * | 9/1986 | Hyman | 351/86 |
| 5,110,198 | * | 5/1992 | Travis et al. | 351/124 |
| 5,390,373 | * | 2/1995 | Flory | 2/430 |
| 5,940,162 | * | 8/1999 | Wong | 351/47 |
| 6,012,811 | * | 1/2000 | Chao et al. | 351/47 |
| 6,076,926 | * | 6/2000 | Kostka | 351/113 |
| 6,098,207 | * | 8/2000 | Burtin | 2/431 |

* cited by examiner

*Primary Examiner*—John J. Calvert
*Assistant Examiner*—Katherine Moran
(74) *Attorney, Agent, or Firm*—Jack Lo

(57) ABSTRACT

The present eye wear is comprised of a pair of lenses, a pair of releasable connectors connected to respective inner ends of the lenses, a pair of temples pivotally connected to respective outer ends of the lenses, and a rigid strap attached between the rear ends of the temples. The strap is positioned below the lenses so as to not interfere with a hairdo or helmet. The inner ends of the lenses are releasably secured together by the connectors. To wear, the lenses are separated from each other and pivoted outwardly, the strap is wrapped around the back of the head, and the lenses are pivoted toward each other and secured together in front of the eyes. The lenses are instantly separable for easily putting on or taking off the eye wear, but they are instantly connectable together for a secure and accurate fit. In a second embodiment, the strap is comprised of an adjustable-length flexible strap.

14 Claims, 4 Drawing Sheets

EYE WEAR WITH SNAP-TOGETHER BRIDGE

BACKGROUND OF THE INVENTION

1. Field of the Invention

This invention relates generally to eye wear.

2. Prior Art

Eye wear includes glasses and goggles. Each one typically includes a pair of lenses fixedly connected by a bridge at the inner ends, and a pair of temples hinged to the respective outer ends of the lenses. The rear ends of the temples are disconnected from each other, so that the temples are foldable against the back of the lenses for storge. The eye wear is put on by opening the temples, positioning them on the sides of the wearer's head, and pushing them through the hair and the respective gaps between the ears and the sides of the head. This procedure is a little cumbersome, and occasionally the wearer is poked in the eye by one of the temples during the process.

A retainer strap is sometimes attached between the temples for hanging the eye wear on the neck when it is not being worn. The strap must be looped over the head, which makes the eye wear even more cumbersome to put on, and may also disturb a hairdo when looping over the head.

Stylish "DOUBLE MONOCLE" sunglasses offered by Chanel depart from the traditional construction of eye wear by not having a bridge. It includes a pair of lenses which are disconnected at their inner ends. A rigid horizontal loop is positioned behind the lenses and connected between their outer ends. The loop includes a pair of temple sections coplanar with a rear section, and a pair of downwardly projecting ear hooks. Because the lenses are completely disconnected at their inner ends, they are difficult or even impossible to be aligned with each other. They would be so loose on the wearer that they cannot be accurately positioned in front of the eyes. The rear section of the loop is positioned high on the back of the head, so that it will interfere with a hairdo or a helmet. The loop is not hinged to the lenses, so that the glasses are difficult to put on.

OBJECTIVES OF THE INVENTION

Accordingly, the objectives of the present eye wear are:

to be easily put on without poking the eye;

to position lenses accurately in front of the eyes;

to be completely stable and secure when worn;

to be easily removed;

to not interfere with a hairdo or helmet when worn; and to conveniently hang around a neck when not being worn.

Further objectives of the present invention will become apparent from a consideration of the drawings and ensuing description.

BRIEF SUMMARY OF THE INVENTION

The present eye wear is comprised of a pair of lenses, a pair of releasable connectors connected to respective inner ends of the lenses, a pair of temples pivotally connected to respective outer ends of the lenses, and a rigid strap attached between the rear ends of the temples. The strap is positioned below the lenses so as to not interfere with a hairdo or helmet. The inner ends of the lenses are releasably secured together by the connectors. To wear, the lenses are separated from each other and pivoted outwardly, the strap is wrapped around the back of the head, and the lenses are pivoted toward each other and secured together in front of the eyes. The lenses are instantly separable for easily putting on or taking off the eye wear, but they are instantly connectable together for a secure and accurate fit. In a second embodiment, the strap is comprised of an adjustable-length flexible strap.

Figure 1:
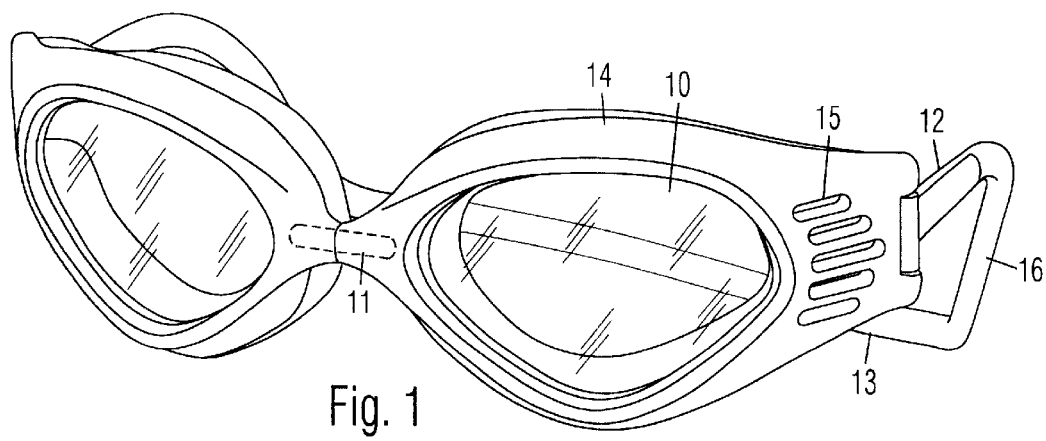
FIG. 1 is a front perspective view of the present eye wear.

| DRAWING REFERENCE NUMERALS | |
|---|---|
| 10. Lenses | 11. Connectors |
| 12. Temples | 13. Rigid Strap |
| 14. Frames | 15. Vents |
| 16. Hooked Portions | 17. Flexible Strap |
| 18. Cinch | 19. Temples |

DETAILED DESCRIPTION OF THE INVENTION

Figure 2:
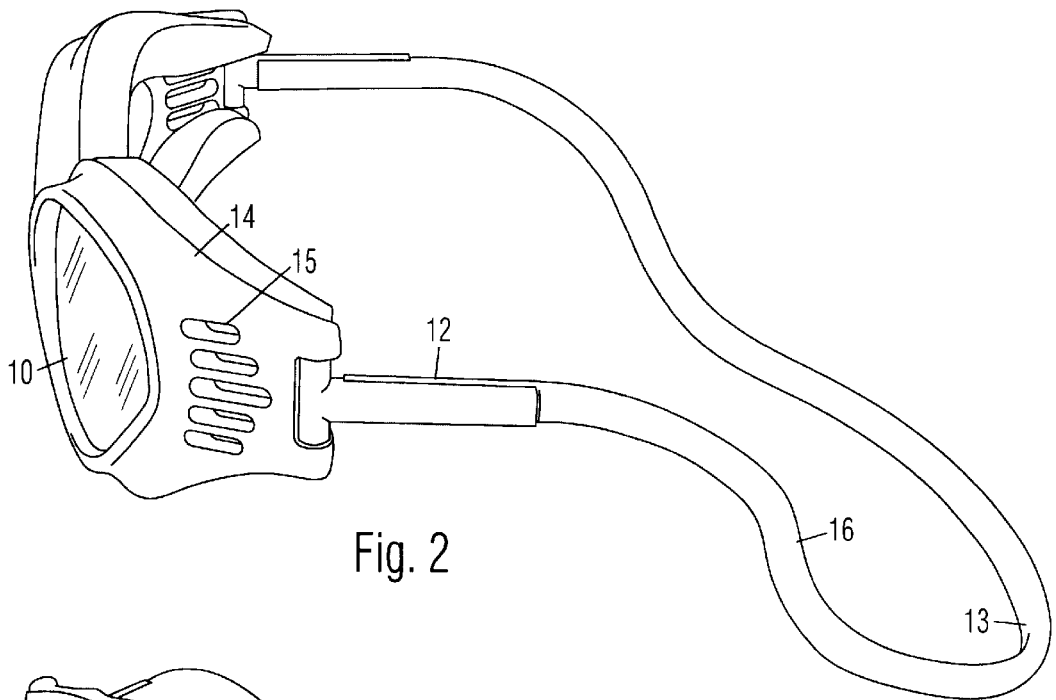
FIG. 2 is a side perspective view thereof.

A first embodiment of the present eye wear is shown in a front perspective view in FIG. 1 and a side perspective view in FIG. 2. It is comprised of a pair of lenses 10, a pair of releasable connectors 11 connected to respective inner ends of lenses 10, a pair of temples 12 connected to respective outer ends of lenses 10, and a generally rigid strap 13 attached between rear ends of temples 12.

Lenses 10 are preferably mounted in respective frames 14 which are provided with vents 15. Connectors 11 are preferably attached to respective inner ends of frames 14. Temples 12 are preferably telescopic for fitting different wearers. Temples 12 are preferably pivoted to the respective outer ends of frames 14. Temples 12 preferably include hooked portions 16 for hooking around the ears. Strap 13 is positioned below lenses 10 so as to avoid interfering with a hairdo or helmet. Strap 13 should be springy enough to retain its shape when released, but are preferably also flexible enough to be bendable to some extent without breaking. Alternatively, strap 13 may be at the same level as temples 12, but at the loss of some advantages.

Alternatively, connectors 11 and temples 12 may be attached directly to lenses 10. Connectors 11 are preferably comprised of magnets, such as neodymium-iron-boron magnets, for maximum convenience when connecting and disconnecting, but they may be any type of releasable connectors, such as latches, hook-and-loop fasteners, etc. When connectors 11 are connected together, they form a bridge between lenses 10. Although the eye wear is shown as a pair of goggles, it may also be a pair of glasses.

Figure 3:
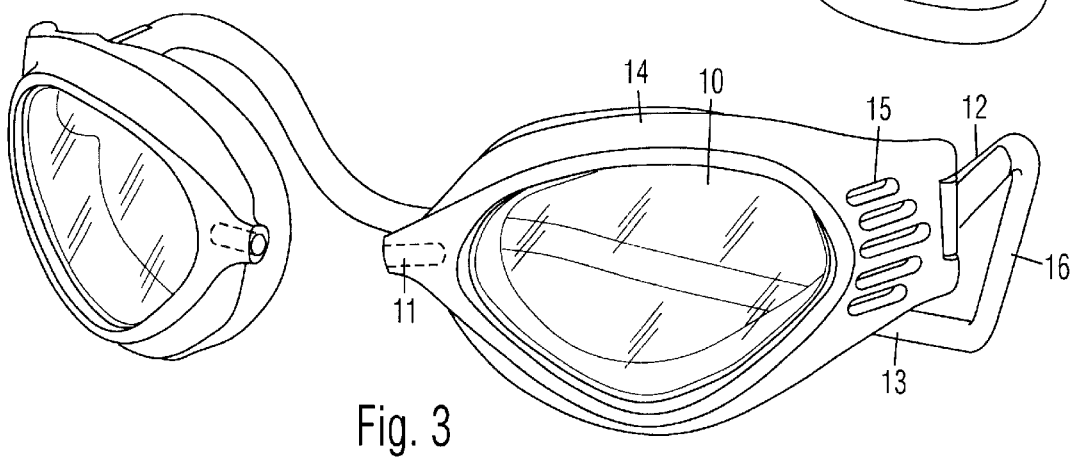
FIG. 3 is a front perspective view thereof when a pair of lenses are separated.
Figure 4:
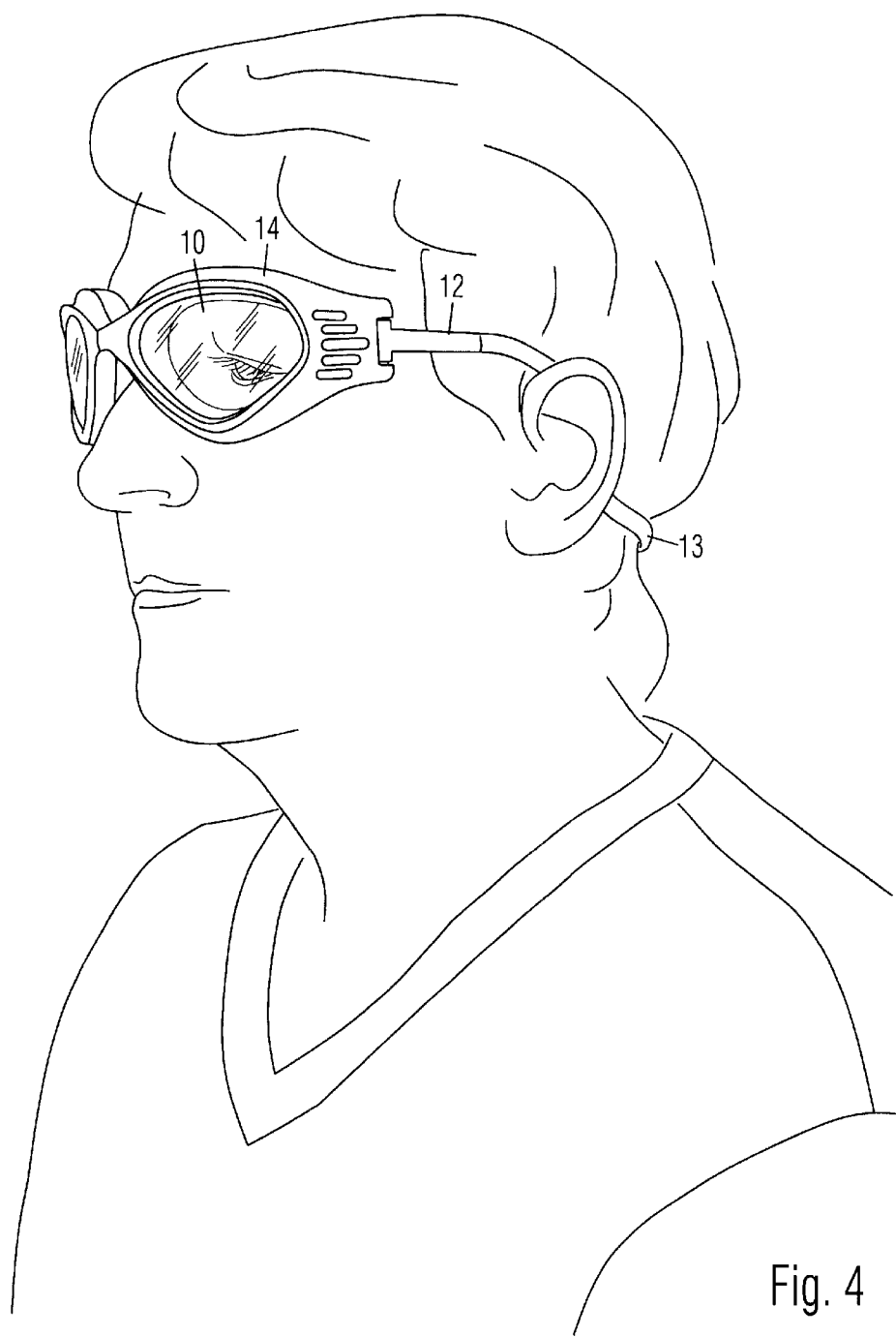
FIG. 4 is a front perspective view thereof when worn on a person.
Figure 5:
FIG. 5 is a front perspective view thereof when hung around the neck of the person.
Figure 6:
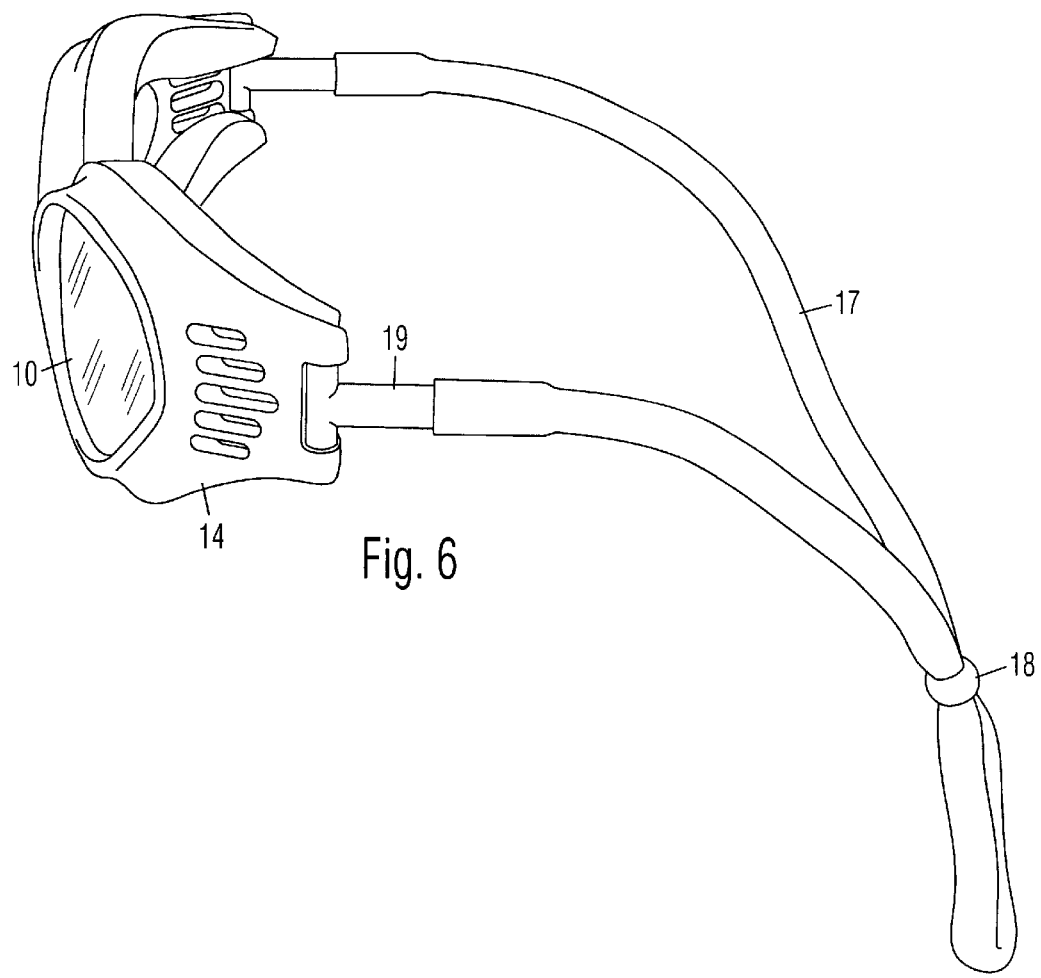
FIG. 6 is a side perspective view of a second embodiment thereof.

The inner ends of lenses 10 are releasably secured together by connectors 11. To wear, lenses 10 are separated from each other and pivoted outwardly, as shown in FIG. 3, strap 13 is wrapped around the back of the head, and lenses 10 are pivoted back toward each other and connected together in front of the eyes, as shown in FIG. 4. The secure connection between lenses 10 ensures that they are accurately positioned in front of the eyes. Because the present eye wear is put on from the back of the head, it will never poke the wearer in the eye. Lenses 10 are instantly separable for easily putting on or taking off the eye wear, but are instantly connectable together for a secure and accurate fit. When the eye wear is not being worn, lenses 10 are separated and hung around the neck under strap 13, as shown in FIG. 5.

In a second embodiment, lenses 10 are connected between their outer ends by a completely flexible strap 17, such as a fabric or rubber strap, which is adjustable in length with a cinch 18 movable there along. Alternatively, strap 17 may be adjusted with other devices, such as a buckle, snaps, etc. Strap 17 is attached to the rear ends of temples 19 as shown, or it may be attached directly to the outer ends of frames 14.

Accordingly, the present eye wear is easily put on without poking the eye. It positions the lenses accurately in front of the eyes. It is completely stable and secure when worn. It is easily removed. It generally does not interfere with a helmet when worn. It can be conveniently hung around a neck when not being worn.

Although the above description is specific, it should not be considered as a limitation on the scope of the invention, but only as an example of the preferred embodiment. Many variations are possible within the teachings of the invention. Therefore, the scope of the invention should be determined by the appended claims and their legal equivalents, not by the examples given.

I claim:

1. An eye wear, comprising:
   a pair of lenses;
   a pair of releasable connectors connected to respective inner ends of said lenses, said connectors being securely connectable together and releasable from each other;
   a pair of temples connected to respective outer ends of said lenses; and
   a strap connected between rear ends of said temples, said strap being rigid enough to generally retain its shape when said connectors are released, and springy enough to be bendable when flexed and rebounding when released;
   wherein when said connectors are released from each other, said inner ends of said lenses are separable from each other so that said eye wear is easy to put on and remove, and when said connectors are connected together, said lenses are secured in position relative to each other for secure and stable positioning in front of a pair of eyes.

2. The eye wear of claim 1, wherein said connectors are comprised of magnets.

3. The eye wear of claim 1, wherein said temples are comprised of telescopic temples for fitting different wearers.

4. The eye wear of claim 1, wherein said temples are pivotally connected to said lenses, so that when said connectors are released from each other, said inner ends of said lenses are pivotable outwardly for making wearing easier.

5. The eye wear of claim 1, further including a pair of frames, said lenses being respectively mounted in said frames, said connectors being attached to respective inner ends of said frames, said temples being attached to respective outer ends of said frames.

6. An eye wear, comprising:
   a pair of lenses;
   a pair of releasable connectors connected to respective inner ends of said lenses, said connectors being securely connectable together and releasable from each other;
   a pair of temples connected to respective outer ends of said lenses, rear ends of said temples being hooked downward for wrapping around a pair of ears; and
   a strap connected between said rear ends of said temples, said strap being rigid enough to generally retain its shape when said connectors are released, and springy enough to be bendable when flexed and rebounding when released, said strap being positioned below said lenses for avoiding interfering with a hairdo or a helmet;
   wherein when said connectors are released from each other, said inner ends of said lenses are separable from each other so that said eye wear is easy to put on and remove, and when said connectors are connected together, said lenses are secured in position relative to each other for secure and stable positioning in front of a pair of eyes.

7. The eye wear of claim 6, wherein said connectors are comprised of magnets.

8. The eye wear of claim 6, wherein said temples are comprised of telescopic temples for fitting different wearers.

9. The eye wear of claim 6, wherein said temples are pivotally connected to said lenses, so that when said connectors are released from each other, said inner ends of said lenses are pivotable outwardly for making wearing easier.

10. The eye wear of claim 6, further including a pair of frames, said lenses being respectively mounted in said frames, said connectors being attached to respective inner ends of said frames, said temples being attached to respective outer ends of said frames.

11. An eye wear, comprising:
    a pair of lenses;
    a pair of magnets connected to respective inner ends of said lenses, said magnets being securely connectable together and releasable from each other; and
    a flexible strap connected between outer ends of said lenses;
    wherein when said magnets are released from each other, said inner ends of said lenses are separable from each other so that said eye wear is easy to put on and remove, and when said magnets are connected together, said lenses are secured in position relative to each other for secure and stable positioning in front of a pair of eyes.

12. The eye wear of claim 11, further including a pair of temples respectively connected to said outer ends of said lenses, said strap being attached between rear ends of said temples.

13. The eye wear of claim 11, further including a pair of frames, said lenses being respectively mounted in said frames, said magnets being attached to respective inner ends of said frames, said straps being connected to respective outer ends of said frames.

14. The eye wear of claim 11, further including a cinch movable along said strap for adjusting a length of said strap.

* * * * *